(12) United States Patent
Shenai-Khatkhate et al.

(10) Patent No.: US 6,939,983 B2
(45) Date of Patent: Sep. 6, 2005

(54) ALKYL GROUP VA METAL COMPOUNDS

(75) Inventors: Deodatta Vinayak Shenai-Khatkhate, Danvers, MA (US); Artashes Amamchyan, Wakefield, MA (US); Michael Brendan Power, Newburyport, MA (US); Ronald L. DiCarol, Jr., Danville, NH (US); James Edward Felton, Hudson, NH (US)

(73) Assignee: Rohm and Haas Electronic Materials, LLC, Marlborugh, MA (US)

( * ) Notice: Subject to any disclaimer, the term of this patent is extended or adjusted under 35 U.S.C. 154(b) by 0 days.

(21) Appl. No.: 10/841,127

(22) Filed: May 7, 2004

(65) Prior Publication Data

US 2005/0033073 A1 Feb. 10, 2005

Related U.S. Application Data

(60) Provisional application No. 60/469,074, filed on May 8, 2003.

(51) Int. Cl.[7] ............................. C07F 9/02; C07F 9/90; C07F 9/94

(52) U.S. Cl. ............................... 556/70; 568/8; 568/16
(58) Field of Search ............................... 556/70; 568/8, 568/16

(56) References Cited

U.S. PATENT DOCUMENTS

| | | | | | |
|---|---|---|---|---|---|
| 3,414,625 | A | * | 12/1968 | Lach et al. | 568/8 |
| 4,611,071 | A | * | 9/1986 | DePriest | 556/70 |
| 5,326,425 | A | * | 7/1994 | Gedridge, Jr. | 117/104 |
| 6,660,874 | B2 | * | 12/2003 | Shenai-Khatkhate et al. | 556/70 |
| 2003/0181746 | A1 | | 9/2003 | Shenai-Khatkhate et al. | 556/42 |

FOREIGN PATENT DOCUMENTS

| EP | 0 839 817 A2 | 5/1998 |
|---|---|---|
| JP | 1995-31617 A | 12/1995 |

* cited by examiner

*Primary Examiner*—Porfirio Nazario-Gonzalez
(74) *Attorney, Agent, or Firm*—S. Matthew Cairns

(57) ABSTRACT

A method of preparing Group VA organometal compounds in high yield and high purity by the reaction of a Grignard reagent with a Group VA metal halide in certain ethereal solvents is provided. A method of preparing Group VA organometal hydrides is also provided.

10 Claims, No Drawings

ALKYL GROUP VA METAL COMPOUNDS

This application claims the benefit of 60/469,074 filed on May 8, 2003.

BACKGROUND OF THE INVENTION

The present invention relates generally to the field of organometallic compounds. In particular, the present invention relates to alkyl Group VA metal compounds which are suitable for use as precursors for chemical vapor deposition.

Metal films may be deposited on surfaces, such as non-conductive surfaces, by a variety of means such as chemical vapor deposition ("CVD"), physical vapor deposition ("PVD"), and other epitaxial techniques such as liquid phase epitaxy ("LPE"), molecular beam epitaxy ("MBE"), and chemical beam epitaxy ("CBE"). Chemical vapor deposition processes, such as metalorganic chemical vapor deposition ("MOCVD"), deposit a metal layer by decomposing organometallic precursor compounds at elevated temperatures, i.e. above room temperature, either at atmospheric pressure or at reduced pressures.

A wide variety of metals may be deposited using such CVD or MOCVD processes. See, for example, Stringfellow, *Organometallic Vapor Phase Epitaxy: Theory and Practice*, Academic Press, $2^{nd}$ Edition, 1999, for an overview of such processes. Organometallic compounds of arsenic, antimony, and bismuth are used to deposit epitaxial films in the semiconductor and related electronic industries. Epitaxial films such as gallium arsenide find applications in optoelectronic devices such as detectors, solar cells, light-emitting diodes ("LED's"), lasers and electronic switching devices such as field effect transistors ("FET's") and high electron mobility FET's ("HEMT's"). Ternary arsenic alloys also exist such as gallium indium arsenide ("GaInAs") and aluminum indium arsenide ("AlInAs"), which are more attractive than GaAs or aluminum gallium arsenide ("AlGaAs") for the most powerful fiber optic systems operating in the 1.3 to 1.55 micron wavelength range. Gallium arsenide phosphide ("GaAsP") is suitable for visible LED's and fiber optic emitters/detectors. Antimony and antimony alloy films are useful in fiber optics communication systems, particularly in the 1.3 and 1.55-micron regions. Antimony-containing semiconductor materials also have commercial applications including detection for seeker, night vision and surveillance devices (infrared detectors) and sources (LED's or lasers). A variety of binary, ternary and quaternary Group III/V semiconductor systems containing antimony have been evaluated for applications in infrared emitters and detectors operating in the 3 to 5 micron and 8 to 12 micron spectral ranges. These wavelength ranges are important since they are natural windows in the atmosphere for infrared transmission. Epitaxial antimony-based Group III/V semiconductors have potential applications in long wavelength detectors and high-speed electronic devices.

Arsine ("$AsH_3$") and phosphine ("$PH_3$") are attractive precursors for MOVPE since they provide arsenic and phosphorus along with hydrogen radicals that can scavenge any carbon-containing radicals generated during the MOVPE growth. However, the highly toxic nature of arsine and phosphine makes handling these gases in cylinders at high pressures dangerous. The threat of their rapid release in large quantities is serious and significantly high facility costs are often incurred to meet the appropriate safety requirements. Thus, there is a need to develop alternative Group VA hydride precursor compounds that are less hazardous than arsine and phosphine. Certain trialkyl Group VA metal compounds, such as trialkyl stibines, have been developed. However, such trialkyl compounds typically have low vapor pressures and higher decomposition temperatures. Such trialkyl compounds also result in carbon incorporation in the grown films. Monoalkyl Group VA dihydride compounds are excellent alternatives as they greatly reduce the amount of carbon incorporated in grown metal films.

For semiconductor and electronic device applications, these Group VA metal alkyls must be highly pure and be substantially free of detectable levels of both metallic impurities, such as silicon and zinc, as well as oxygenated impurities. Oxygenated impurities are typically present from the solvents used to prepare such organometallic compounds, and are also present from other adventitious sources of moisture or oxygen.

Methods of preparing monoalkyl arsines and phosphines by reacting arsine or phosphine gas with an alkene in the presence of a catalyst are known. Such methods are favored commercially as they require the handling of arsine gas or phosphine gas, which are both very toxic.

Grignard type syntheses of alkyl Group VA metal compounds are also known. For example, arsenic trihalide or phosphorus trihalide is reacted with an alkyl Grignard reagent to form a monoalkyl arsenic or monoalkyl phosphorus compound which is subsequently reduced to form monoalkyl arsine ($RAsH_2$) or monoalkyl phosphine ($RPH_2$). Such reactions are carried out in low boiling ethereal solvents, such as diethyl ether. While these Grignard reactions work well, the products are typically contaminated with residual ethereal solvent, and require extensive purification to remove the ethereal solvent. Even with such purification procedures, trace ethereal solvents remain in the monoalkyl arsines and phosphines. This remaining ethereal solvent, which is an oxygenated impurity, is undesirable for chemical vapor deposition processes.

Attempts have been made to reduce the amount of ethereal solvent in monoalkyl arsines and phosphines. For example, EP 839 817 A2 (Murakoshi et al.) discloses a method of preparing monoalkyl-arsines and -phosphines by first reacting an alkyl Grignard reagent with arsenic trihalide or phosphorus trihalide in diethyl ether to form an alkyl arsenic or phosphorus dihalide, removing the diethyl ether to leave a solid, adding diglyme (b.p. 160° C.) to the solid, reducing the alkyl arsenic or phosphorus dihalide with lithium aluminum hydride to form alkyl arsine or alkyl phosphine, and then distilling the alkyl arsine or alkyl phosphine. The distilled alkyl arsine and alkyl phosphine was found to contain ca. 9% or greater of diglyme. The alkyl arsine or phosphine product was then treated with a zeolite for seven days in order to reduce the amount of impurities. Such method is not practical commercially due to the extra cost of materials and long times required.

Accordingly, methods of preparing Group VA metal alkyl compounds in high yields and that are substantially free of both metallic and oxygenated impurities for use as precursor compounds for CVD are desired.

SUMMARY OF THE INVENTION

It has been found that Group VA organometal compounds can be prepared in high yield and in high purity using Grignard reactions. Such reactions are carried out in certain ether-containing solvents. Group VA organometal compounds produced by this method are extremely pure and substantially free of oxygenated impurities.

The present invention provides a method of preparing a Group VA organometal compound including the step of reacting one or more organomagnesium halide compounds with one or more Group VA metal halide compounds in an ethereal solvent, wherein the ethereal solvent has a boiling point of ≧175° C.

Also provided by the present invention is a method for preparing Group VA organometal hydride compounds including the steps of: a) reacting one or more organomagnesium halide compounds with one or more Group VA metal halide compounds in an ethereal solvent to form one or more Group VA organometal halide compounds, wherein the ethereal solvent has a boiling point of ≧175° C.; and b) contacting the one or more Group VA organometal halide compounds with a reducing agent to form one or more Group VA organometal hydride compounds.

DETAILED DESCRIPTION OF THE INVENTION

As used throughout this specification, the following abbreviations shall have the following meanings, unless the context clearly indicates otherwise: ° C.=degrees centigrade; NMR=nuclear magnetic resonance; mol=moles; b.p.= boiling point, g=gram; L=liter; M=molar; ca.= approximately; μm=micron=micrometer; mL=milliliter; Ph=phenyl; t-Bu=tertiary-butyl; i-Pr=iso-propyl; Me=methyl; and Et=ethyl.

"Halogen" refers to fluorine, chlorine, bromine and iodine and "halo" refers to fluoro, chloro, bromo and iodo. Likewise, "halogenated" refers to fluorinated, chlorinated, brominated and iodinated. "Alkyl" includes linear, branched and cyclic alkyl. Unless otherwise noted, all amounts are percent by weight and all ratios are molar ratios. All numerical ranges are inclusive and combinable in any order except where it is clear that such numerical ranges are constrained to add up to 100%.

The present invention provides Group VA organometal compounds that are substantially free of both metallic and oxygenated impurities. By "substantially free" it is meant that the Group VA organometal compounds contain less than 0.5 ppm of such impurities, and preferably less than 0.25 ppm. Such compounds are particularly suitable for use in chemical vapor deposition processes.

The term "Group VA organometal compound" refers to any Group VA metal compound containing one or more organic moieties bonded to the Group VA metal. There is no particular restriction on the organic moiety, and such may include, without limitation, aryl, alkyl, alkenyl, and alkynyl. Exemplary organic moieties include $(C_1-C_{12})$alkyl, $(C_2-C_{12})$alkenyl, $(C_2-C_{12})$alkynyl, and $(C_6-C_{20})$aryl. The organic moiety may optionally be substituted, such as by replacing one or more hydrogens on the organic moiety with one or more substituent groups. Exemplary substituent groups include $(C_1-C_{10})$alkyl, amino, $(C_1-C_{10})$alkylamino, and di$(C_1-C_{10})$alkylamino. Suitable Group VA metals include antimony ("Sb"), arsenic ("As"), bismuth ("Bi") and phosphorus ("P"). Particularly suitable Group VA metals are arsenic and phosphorus. Exemplary Group VA organometal compounds include those of the formula $MRY^1Y^2$, wherein M is a Group VA metal, R=$(C_1-C_{12})$alkyl, $(C_2-C_{12})$alkenyl, $(C_2-C_{12})$alkynyl, and $(C_6-C_{20})$aryl; and $Y^1$ and $Y^2$ are independently selected from hydrogen, halogen, $(C_1-C_{12})$alkyl, $(C_2-C_{12})$alkenyl, $(C_2-C_{12})$alkynyl, and $(C_6-C_{20})$aryl.

Group VA organometal compounds are prepared according to the present invention by reacting one or more organomagnesium halide compounds with one or more Group VA metal halide compounds in an ethereal solvent, wherein the ethereal solvent has a boiling point of ≧175° C. A wide variety of organomagnesium halide compounds (i.e. Grignard reagents) may suitably be used in the present invention. The organo moiety in such Grignard reagents may be any suitable organic residue, such as alkyl, alkenyl, alkynyl and aryl. In general, such compounds have the formula $R^1MgX$, wherein $R^1$ is $(C_1-C_{12})$alkyl, $(C_2-C_{12})$alkenyl, $(C_2-C_{12})$alkynyl, and $(C_6-C_{20})$aryl; and X is a halogen. Exemplary halogens for X include, without limitation, bromine or chlorine. The group for $R^1$ may optionally be substituted, such as with any of the groups described above for the Group VA organometal compounds. The organomagnesium compounds are generally commercially available, such as from Aldrich (Milwaukee, Wis.), or may be prepared by a variety of methods known in the literature. For example, an alkyl magnesium halide compound may be prepared by combining an alkyl halide with magnesium metal in an ethereal solvent.

A wide variety of Group VA metal halide compounds may be used. Such compounds contain at least one halogen bonded to the Group VA metal, but may contain 2 or three halogens. If the Group VA metal halide compounds contain 2 or 3 halogens, the halogens may be the same or different. Exemplary Group VA metal halide compounds have the formula $R^2R^3MX^1$, where $X^1$ is a halogen; M is a Group VA metal; and $R^2$ and $R^3$ are independently selected from hydrogen, halogen, $(C_1-C_{12})$alkyl, $(C_2-C_{12})$alkenyl, $(C_2-C_{12})$alkynyl, and $(C_6-C_{20})$aryl. Any of the organic groups for $R^2$ and $R^3$ may be optionally substituted as described above. The Group VA metal halide compounds are generally commercially available, such as from Gelest (Tullytown, Pa.) or may be prepared by methods known in the literature. Suitable literature methods include, but are not limited to, Grignard reactions, organolithium reactions, and transalkylation reactions such as with an alkyl Group III compound.

In one embodiment, one or more Group VA metal trihalides are used. Such trihalide compounds have the formula $MX_3$ wherein M is a Group VA metal and each X is independently chlorine, bromine, fluorine or iodine. Preferably, the halogen is chlorine, bromine or iodine. Exemplary Group VA metal trihalide compounds include, but are not limited to, antimony trichloride, antimony tribromide, antimony triiodide, arsenic trichloride, arsenic tribromide, arsenic triiodide, bismuth trichloride, bismuth tribromide, bismuth triiodide, phosphorus trichloride, phosphorus tribromide, phosphorus triiodide, and mixtures thereof. Group VA metal trichlorides are particularly suitable. It will be appreciated that mixed halide compounds may also be advantageously used in the present invention.

The equivalent ratio of the Grignard reagent to the Group VA metal halide compound is typically from 0.8:1 to 1.2:1 and more typically from 0.9:1 to 1.1:1, based on each halide in the Group VA metal halide compound that is to be replaced with an organic moiety. For example, a Group VA metal trihalide could be reacted with approximately 1, 2 or 3 equivalents of organomagnesium compound depending upon the number of halides to be replaced.

The present process is performed in an ethereal solvent having a boiling point of ≧175° C., as measured at atmospheric pressure. Exemplary ethereal solvents have a boiling point of ≧180° C., and more exemplary ethereal solvents have a boiling point of ≧200° C. Suitable ethereal solvents include, but are not limited to, butyl diglyme, diethylene glycol diethyl ether, allyl 3-methylphenyl ether, allyl 4-methylphenyl ether, allyl 2-methylphenyl ether, benzyl phenyl ether, bis(2-ethylhexyl) ether, bis (2-ethylphenyl) ether, bis(2-methoxyphenyl) ether, bis (2-methylphenyl)

ether, bis(3-methylphenyl) ether, bis(4-methylphenyl) ether, bis(1-phenylethyl) ether, bis(2-phenylethyl) ether, butyl phenyl ether, dicyclohexyl ether, didecyl ether, diethylene glycol dibutyl ether, diheptyl ether, dihexyl ether, dinonyl ether, dioctyl ether, dibenzyl ether, ethylene glycol dibutyl ether, 2-ethylhexyl vinyl ether, heptyl phenyl ether, hexadecyl vinyl ether, hexyl phenyl ether, octyl phenyl ether, pentyl phenyl ether, propyl 1-naphthyl ether, propyl 2-naphthyl ether, tetraethylene glycol dimethyl ether, triethylene glycol dimethyl ether, and mixtures thereof. The ethereal solvent may be a single solvent or a solvent mixture. Such solvent mixture contains at least one ether solvent and may contain one or more other organic solvents.

A wide variety of other organic solvents may be used, provided that they are miscible with the one or more ethereal solvents used. Suitable other organic solvents include, but are not limited to, hydrocarbons and aromatic hydrocarbons. Exemplary organic solvents include benzene; alkyl substituted benzenes such as toluene, xylene, and ($C_4$–$C_{20}$)alkyl benzenes such as ($C_{10}$–$C_{12}$)alkyl benzenes and ($C_{10}$–$C_{20}$) alkyl biphenyls; and aliphatic hydrocarbons such as pentane, hexane, heptane, octane, decane, dodecane, squalane, cyclopentane, cyclohexane, and cycloheptane; and mixtures thereof.

In general, the ethereal solvents are deoxygenated prior to use. The solvents may be deoxygenated by a variety of means, such as purging with an inert gas, degassing the solvent in vacuo, or a combination thereof. Suitable inert gases include argon, nitrogen and helium.

Typically, the ethereal solvent and the one or more Group VA metal halide compounds are added to a reaction vessel. The vessel is cooled, such as from –10° to –78° C. To the cooled the solvent/Group VA metal halide compound mixture are added the one or more organomagnesium halide compounds. After addition is complete, the reaction vessel is generally allowed to warm to room temperature. If desired, the unwanted magnesium dihalide byproduct may be separated from the reaction mixture by a variety of means, such as filtration or sublimation. The Group VA organometal compounds are isolated and may be used as is or may be further purified, such as by distillation. In an alternate embodiment, the Group VA organometal compounds may be reacted further without separation form the reaction mixture, such as in the formation of Group VA metal hydrides.

It will be appreciated by those skilled in the art that if the starting Group VA metal halide compound has 2 or 3 halogens that are to be replaced with organic moieties, such moieties may be the same or different. Such halogens may be replaced all in one reaction or one or two halogens may be replaced in each of successive reactions. For example, a Group VA metal dihalide may be reacted with 2 equivalents of organomagnesium halide to provide a Group VA organo metal compound containing 2 organic moieties. Alternatively, a Group VA metal dihalide may be reacted with 1 equivalent of a first organomagnesium halide and then subsequently reacted with 1 equivalent of a second organomagnesium halide.

An advantage of the present invention is that the Group VA organometal compounds separated from the present ethereal solvents are substantially free of ether, i.e. they contain less than 0.5 ppm of ether. Such compounds may be used as precursors for chemical vapor deposition processes.

When the Group VA organometal compound contains one or more halogens, such compound can easily be converted to a Group VA metal hydride compound. In such reaction, the Group VA organometal compound containing one or more halogens is reduced. Such reduction may optionally be performed in the presence of a tertiary amine.

Group VA organometal halides may be reduced to form Group VA organometal hydrides. In one embodiment, Group VA organometal monohalides are reduced to form Group VA organometal monohydrides. Exemplary Group VA organometal monohalides are those of the formula $R_2MX$, wherein each R is independently hydrogen, ($C_1$–$C_{12}$)alkyl, amino-substituted ($C_1$–$C_{12}$)alkyl, aryl, substituted aryl, ($C_2$–$C_{12}$)alkenyl, or ($C_2$–$C_{12}$)alkynyl; M is a Group VA metal; and each X is independently fluorine, chlorine, bromine or iodine; provided that at least one R is not hydrogen. Exemplary Group VA metals are arsenic and phosphorus. X is typically chlorine, bromine or iodine.

In another embodiment, Group VA organometal dihalides are reduced to form Group VA organometal dihydrides. Exemplary Group VA organometal dihalides include, but are not limited to, those having the general formula $R^4MX_2$, wherein $R^4$ is ($C_1$–$C_{12}$)alkyl, amino-substituted ($C_1$–$C_{12}$) alkyl, aryl, substituted aryl, ($C_2$–$C_{12}$)alkenyl, or ($C_2$–$C_{12}$) alkynyl; M is a Group VA metal; and each X is independently fluorine, chlorine, bromine or iodine. Exemplary Group VA metals are arsenic and phosphorus. X is typically chlorine, bromine or iodine. In general, R is ($C_1$–$C_8$)alkyl and more generally ($C_1$–$C_6$)alkyl, ($C_2$–$C_{10}$)alkenyl,.

Particularly suitable Group VA organometal dihalides include, but are not limited to, methyl arsenic dichloride, ethyl arsenic dichloride, n-propyl arsenic dichloride, iso-propyl arsenic dichloride, n-butyl arsenic dichloride, iso-butyl arsenic dichloride, tert-butyl arsenic dichloride, cyclohexyl arsenic dichloride, methylcyclohexyl arsenic dichloride, methyl arsenic dibromide, ethyl arsenic dibromide, n-propyl arsenic dibromide, iso-propyl arsenic dibromide, n-butyl arsenic dibromide, iso-butyl arsenic dibromide, tert-butyl arsenic dibromide, cyclohexyl arsenic dibromide, methyl phosphorus dichloride, ethyl phosphorus dichloride, n-propyl phosphorus dichloride, iso-propyl phosphorus dichloride, n-butyl phosphorus dichloride, iso-butyl phosphorus dichloride, tert-butyl phosphorus dichloride, cyclopentyl phosphorus dichloride, cyclohexyl phosphorus dichloride, methyl phosphorus dibromide, ethyl phosphorus dibromide, n-propyl phosphorus dibromide, iso-propyl phosphorus dibromide, n-butyl phosphorus dibromide, iso-butyl phosphorus dibromide, tert-butyl phosphorus dibromide, cyclohexyl phosphorus dibromide, methylcyclohexyl phosphorus dibromide, and mixtures thereof It will be appreciated that mixed halide compounds may also be advantageously used in the present invention.

Other suitable Group VA organometal dihalides include those having the formula $X_2M^1R^5M^2X_2$, wherein $M^1$ and $M^2$ are independently selected from arsenic and phosphorus, each X is independently selected from fluorine, chlorine, bromine and iodine, and $R^5$ is an alkylene or arylene group. Typically, the groups for $R^5$ are free of oxygen substitution. Suitable groups for $R^5$ include, but are not limited to: ($C_1$–$C_{10}$)alkylene such as methylene, ethylene, propylene, butylene and the like; ($C_8$–$C_{20}$)aralkylene such as p-xylylene; and ($C_6$–$C_{20}$)arylene such as phenylene, biphenylene and naphthylene.

Group VA organometal hydrides are prepared by contacting one or more Group VA organometal halides with a reducing agent. In general, a reducing agent and a suitable solvent are combined in a reaction vessel. Optionally, a tertiary amine may be used in the reduction step. Suitable solvents for the reducing agent are any that do not react with the reducing agent. A wide variety of solvents are suitable for the reduction reaction, including, without limitation, hydrocarbons such as aromatic hydrocarbons and aliphatic hydrocarbons, ethers, and solvent mixtures. In one embodiment, the solvent is an ethereal solvent having a boiling point of ≧175° C. Exemplary ethers include those described above for use in the organomagesium halide reaction. Such solvents are typically deoxygenated by any of the methods described above. In another embodiment, the reducing agent is present in the same solvent as the Group VA organometal halide compound. The one or more Group VA organometal halides are typically combined with a suitable solvent, such as any of the ethers described above, and added to the reducing agent solution in a dropwise manner. Typically, the reduction may be performed at a wide range of temperatures. Suitable temperatures are from below ambient temperature to 90° C. Alternate reduction processes will be apparent to those skilled in the art.

A wide variety of reducing agents may be used in the present invention. Exemplary reducing agents include, without limitation, borohydride reducing agents such as sodium borohydride and lithium borohydride; aluminum hydride reducing agents such as lithium aluminum hydride and $NaAlH_2(OCH_2CH_2OCH_3)_2$; and borane reducing agents such as dimethylamine borane, cyclohexylamine borane, morpholine borane.

When a tertiary amine is used in the reduction step, the tertiary amine, organic solvent and reducing agent may be combined in any order prior to reacting with the Group VA organometal halide. The molar amounts of the tertiary amine and the amount of the reducing agent used depend upon the number of halogens in the Group VA organometal compound to be reduced. For Group VA organometal dihalides, the tertiary amine is generally present in twice the molar amount of the Group VA organometal dihalide compound, although other suitable amounts may be used. Likewise, the reducing agent is typically also present in twice the molar amount of Group VA organometal dihalide compound, but other suitable amounts may be used.

Any tertiary amine may suitably be used. Suitable tertiary amines include, but are not limited to, poly(tertiary amines) and amines having the general formula $NR^4R^5R^6$, wherein $R^4$, $R^5$ and $R^6$ are independently selected from $(C_1-C_6)$ alkyl, di$(C_1-C_6)$alkylamino-substituted $(C_1-C_6)$alkyl, and phenyl and wherein $R^4$ and $R^5$ may be taken together along with the nitrogen to which they are attached to form a 5–7 membered heterocyclic ring. Such heterocyclic ring may be aromatic or non-aromatic. Exemplary tertiary amines include, but are not limited to: trimethylamine; triethylamine; tri-n-propylamine; tri-n-butylamine; tri-iso-propylamine; tri-iso-butylamine; dimethylaminocyclohexane; diethylaminocyclohexane; dimethylaminocyclopentane; diethylaminocyclopentane; N-methylpyrrolidine; N-ethylpyrrolidine; N-n-propylpyrrolidine; N-iso-propylpyrrolidine; N-methylpiperidine; N-ethylpiperidine; N-n-propylpiperidine; N-iso-propylpiperidine; N,N'-dimethylpiperazine; N,N'-diethylpiperazine; N,N'-dipropylpiperazine; N,N,N',N'-tetramethyl-1,2-diaminoethane; pyridine; pyrazine; pyrimidine; N,N,N',N'-tetramethylethylene diamine; N,N,N',N'-tetraethylethylene diamine; N,N,N',N'-tetramethylpropylenediamine; N,N,N',N'-tetraethylpropylene diamine; N,N,N',N'-tetramethylbutylene diamine; N,N,N',N'-tetraethylbutylene diamine; 1,5-tetramethyldiaminopentane; 1,5-tetraethyldiaminopentane; N,N,N',N'-tetramethylhexamethylene diamine; 1,7-tetramethyldiaminoheptane; 1,7-tetraethyldiaminoheptane; 1,8-tetramethyldiaminooctane; 1,8-tetraethyldiaminooctane; 1,9-tetramethyldiaminononane; 1,9-tetraethyldiaminononane; 1,10-tetramethyldiaminodecane; 1,10-tetraethyldiaminodecane; 1,12-tetramethyldiaminododecane; 1,12-tetraethyldiaminododecane; pentamethyl diethylenetriamine; and mixtures thereof. More exemplary tertiary amines include trimethylamine, triethylamine, tri-n-propylamine, tri-iso-propylamine, and tri-n-butylamine. It will be appreciated by those skilled in the art that more than one tertiary amine may be used in the present invention. Such tertiary amines are generally commercially available from a variety of sources. Such tertiary amines may be used as is or, preferably further purified prior to use.

The specific tertiary amine and organic solvent used depend upon the particular Group VA organometal hydride compound desired. For example, the organic solvent and tertiary amine may be selected such that they are more volatile or less volatile than the desired Group VA organometal hydride compound. Such differences in volatility provide easier separation of the Group VA organometal hydride compound from both the amine and organic solvent. The Group VA organometal hydride compounds thus produced may be suitably purified by a variety of techniques, such as, but not limited to, distillation, recrystallization or mixtures of such techniques.

A wide variety of Group VA organometal hydride compounds may be produced by the present invention. Exemplary Group VA organometal dihydride compounds have the formula $RMH_2$, wherein M is a Group VA metal; and R is $(C_1-C_{10})$alkyl, amino-substituted $(C_1-C_{10})$alkyl, aryl or substituted aryl. The terms "substituted aryl" and "amino-substituted $(C_1-C_{10})$alkyl" are as defined above. It is preferred that monoalkyl arsines (i.e. $RAsH_2$) and monoalkyl phosphines (i.e. $RPH_2$) are produced by this method. Particularly useful monoalkyl arsines and monoalkyl phosphines are $(C_1-C_6)$alkyl arsines and $(C_1-C_6)$alkyl phosphines. Suitable monoalkyl arsines and monoalkyl phosphines include, but are not limited to: methyl arsine, ethyl arsine, n-propyl arsine, iso-propyl arsine, n-butyl arsine, iso-butyl arsine, tert-butyl arsine, cyclohexyl arsine, methylcyclohexyl arsine, cyclopentyl arsine, methyl phosphine, ethyl phosphine, n-propyl phosphine, iso-propyl phosphine, n-butyl phosphine, iso-butyl phosphine, tert-butyl phosphine, cyclohexyl phosphine, methylcyclohexyl phosphine, cyclopentyl phosphine, and the like. Other suitable compounds include, but are not limited to, phenyl arsine, phenyl phosphine, dimethylaminophenyl arsine, and dimethylaminophenyl phosphine.

In an alternate embodiment, suitable Group VA organometal dihydrides produced by the present invention include, but are not limited to: bisphosphino methane $(H_2PCH_2PH_2)$; 1,2-bisphosphino ethane $(H_2PCH_2CH_2PH_2)$; 1,3-bisphosphino propane $(H_2PCH_2CH_2CH_2PH_2)$; bisphosphino benzenes $(H_2PC_6H_4PH_2)$ such as 1,4-bisphosphino benzene and 1,2-bisphosphino benzene; 1,4-bisphosphinomethyl benzene $(H_2PCH_2C_6H_4CH_2PH_2)$; bisarseno methane $(H_2AsCH_2AsH_2)$, bisarseno ethane $(H_2AsCH_2CH_2AsH_2)$, 1,3-bisarseno propane $(H_2AsCH_2CH_2CH_2AsH_2)$, and bisarseno benzene $(H_2AsC_6H_4AsH_2)$.

Accordingly, the present invention provides a method for preparing Group VA organometal hydride compounds including the steps of: a) reacting one or more organomagnesium halide compounds with one or more Group VA halide compounds in an ethereal solvent to form one or more Group VA organometal halide compounds, wherein the ethereal solvent has a boiling point of ≧175° C.; and b) reducing the one or more Group VA organometal halide compounds by contact with one or more reducing agents. Such reduction step may optionally be performed in the presence of a tertiary amine.

In one embodiment, the one or more organomagnesium halide compounds is reacted with the one or more Group VA halide compounds and then the reaction mixture is added to the one or more reducing agents. The resulting Group VA organometal hydride compounds are then separated from the reaction mixture, such as by distillation.

In another embodiment, the reduction of the one or more Group VA organometal halides is performed in a continuous or semi-continuous manner. In such process, the Group VA organometal halide and reducing agent are delivered separately to a reaction zone which is maintained at a predetermined temperature. The temperature is selected such that the reduction reaction progresses and the Group VA organometal hydride product is separated. For example, the Group VA organometal hydride may be collected at the outlet of the reaction zone while byproducts are removed from the base of the reaction zone.

An advantage of the present invention is that Group VA organometal hydride compounds can be prepared that are substantially free of ethereal solvents, and preferably free of ethereal solvents. A further advantage is that such Group VA organometal hydride compounds are substantially free of metallic impurities such as zinc and silicon, and preferably free of silicon and zinc. By "substantially free" it is meant that the compounds contain less than 0.5 ppm of such impurities, and preferably less than 0.25 ppm. Thus, Group VA organometal hydride compounds prepared from Group VA organometal halide compounds are substantially free of zinc and silicon, and preferably free of zinc, silicon, and ethereal solvents.

The Group VA organometal compounds are particularly suitable for use as precursors in CVD, and particularly MOCVD and metalorganic vapor phase epitaxy ("MOVPE"), particularly for MOVPE of compound semiconductors. These compounds are useful for depositing gallium arsenide films, indium phosphide films, aluminum gallium arsenide films, and the like. Such films are useful in the manufacture of electronic devices, such as integrated circuits, and optoelectronic devices.

Films of Group VA metals are typically deposited by first placing the desired Group VA organometal compound, i.e. source compound or precursor compound, in a bubbler having an outlet connected to a deposition chamber. Suitable Group VA organometal compounds include the present Group VA organometal halides as well as the present Group VA organometal hydrides, as well as other Group VA organometal compounds prepared by the present Grignard reaction. A wide variety of bubblers may be used, depending upon the particular deposition apparatus used. The source compound is maintained in the bubbler as a liquid or solid. Solid source compounds are typically vaporized or sublimed prior to transportation to the deposition chamber. The source compound is typically transported to the deposition chamber by passing a carrier gas through the bubbler. Suitable carrier gasses include nitrogen, hydrogen, and mixtures thereof. In general, the carrier gas is introduced below the surface of the source compound, and bubbles up through the source compound to the headspace above it, entraining or carrying vapor of the source compound in the carrier gas. The entrained or carried vapor then passes into the deposition chamber.

The deposition chamber is typically a heated vessel within which is disposed at least one, and possibly many, substrates. The deposition chamber has an outlet, which is typically connected to a vacuum pump in order to draw by-products out of the chamber and to provide a reduced pressure where that is appropriate. MOCVD can be conducted at atmospheric or reduced pressure. The deposition chamber is maintained at a temperature sufficiently high to induce decomposition of the source compound. The typical deposition chamber temperature is from 300° to 1200° C., the exact temperature selected being optimized to provide efficient deposition. Optionally, the temperature in the deposition chamber as a whole can be reduced if the substrate is maintained at an elevated temperature, or if other energy such as radio frequency ("RF") energy is generated by an RF source.

Suitable substrates for deposition, in the case of electronic device manufacture, may be silicon, gallium arsenide, indium phosphide, and the like. Such substrates are particularly useful in the manufacture of integrated circuits.

Deposition is continued for as long as desired to produce a film having the desired properties. Typically, the film thickness will be from several hundred to several thousand angstroms or more when deposition is stopped.

Thus, the present invention provides a method for depositing a film of a Group VA metal on a substrate including the steps of: a) conveying a Group VA organometal source compound in the gaseous phase to a deposition chamber containing the substrate; b) decomposing the Group VA organometal source compound in the deposition chamber; and c) depositing a film of the Group VA metal on the substrate.

The present invention further provides a method for manufacturing an electronic device including the step of depositing a film of a Group VA metal on an electronic device substrate including the steps of: a) conveying a Group VA organometal source compound in the gaseous phase to a deposition chamber containing the substrate; b) decomposing the Group VA organometal source compound in the deposition chamber; and c) depositing a film of the Group VA metal on the substrate. Suitable electronic devices include, but are not limited to, integrated circuits and light emitting diodes ("LEDs").

The following examples are expected to illustrate various aspects of the present invention, but are not intended to limit the scope of the invention. All manipulations are performed in an inert atmosphere, typically under an atmosphere of dry nitrogen.

EXAMPLE 1

A 5-L stainless steel reactor is equipped with a motorized stirrer, a reflux condenser and a pressure equalizing addiition funnel. To this reactor is charged 150 g of phosphorus trichloride ($PCl_3$) dissolved in 600 mL of butyl diglyme. To the reactor, 1100 mL of tert-butylMgCl (1 M solution in butyldiglyme) is added in a dropwise manner ensuring that the temperature does not exceed 40° C., to produce t-$BuPCl_2$. Once the reaction mass attains room temperature, it is added slowly to a suspension of $LiAlH_4$ (50 g) in butyl diglyme (200 mL). Upon complete addition, the reaction mass is allowed to cooled to room temperature. The addition funnel and reflux condenser are then removed, and the reactor is next equipped with a U-tube connected to a receiver and reflux condenser. The setup is evacuated to 1 mm Hg in order to commence the distillation of crude product into a receiver maintained at −78° C. After the crude product is collected, it is then subjected to atmospheric pressure distillation in a setup composed of a distillation flask equipped with 2 foot (61 cm) distillation column packed with stainless steel packing and connected to a distillation head and stainless steel receiver. To the distillation flask is added $AlCl_3$ (2 g) and KF (1 g), and the setup is evacuated and backfilled with nitrogen prior to transferring the crude product. The final product, tert-butylphosphine (t-BuPH$_2$), is obtained in 82% yield after intentionally discarding the forerun comprised of the first fraction (10%). The product is analyzed by FT-NMR and ICP-OES to assess its final purity at the level of 99.999% (total impurity <5 ppm).

EXAMPLE 2

The procedure of Example 1 is repeated except that arsenic trichloride ($AsCl_3$ (110 g)) is used instead of $PCl_3$. The product, tert-butylarsine (t-BuAsH$_2$), is obtained in >75% yield.

EXAMPLE 3

The procedure of Example 1 is repeated except that the intermediate t-BuPCl$_2$ is separated from the reaction mixture by vacuum sublimation following. This product is then redissolved in butyl diglyme and this solution is then added to the LiAlH$_4$ suspension in butyl diglyme as described in Example 1.

EXAMPLE 4

The procedure of Example 3 is repeated using the reaction of Example 2.

EXAMPLE 5

The procedure of Example 1 is repeated except that the intermediate t-BuPCl$_2$ is separated from the reaction mixture by vacuum sublimation and then redissolved in butyl diglyme. This solution is then reacted with a suspension of LiAlH$_4$ in butyl diglyme (50 g in 200 mL butyl diglyme) in a continuous manner. The reagent streams are transferred independently and mixed in a tubular reactor equipped with a distillation column that is maintained at 80 to 95° C. This tubular reactor is connected to a boiler (containing 1L butyl diglyme maintained at 90 to 100° C.) and a waste receiver at its base via an adopter. The reactor is equipped with a Claisen head condenser and a product receiver at the top. The reactor is "pre-conditioned" with anhydrous butyl diglyme (250 mL) prior to the continuous reduction step. The addition rates of the reagents are maintained at around 100 g per hour, and maintaining an excess of reducing agent at all times. The expected product, t-BuPH$_2$, is collected in a continuous manner as the addition progresses. Crude t-BuPH$_2$ is further purified by fractional distillation using the procedure described in Example 1.

EXAMPLE 6

The procedure of Example 5 is repeated except that $AsCl_3$ (110 g) is used instead of $PCl_3$ and the expected product is t-butylarsine.

EXAMPLE 7

The procedure of Example 1 is repeated except that the following reagents and solvents are used and the reduction step is not performed. The expected products are also listed in the following table.

| Group VA Metal Halide | Grignard Reagent | Solvent | Product |
|---|---|---|---|
| $PCl_3$ | i-PrMgBr | Butyl diglyme | i-PrPCl$_2$ |
| $PCl_3$ | i-PrMgBr | Tetraglyme | (i-Pr)$_2$PCl |
| $AsCl_3$ | EtMgCl | Bis(2-ethylhexyl) ether | EtAsCl$_2$ |
| $PCl_3$ | t-BuMgBr | Tetraglyme | t-BuPCl$_2$ |
| PhAsCl$_2$ | AllylMgBr | Dicyclohexyl ether | Ph(allyl)AsCl |
| Me$_2$PCl | t-BuMgBr | Triethylene glycol dimethyl ether | Me$_2$(t-Bu)P |
| $AsCl_3$ | MeMgBr | Dihexyl ether | MeAsCl$_2$ |
| MeAsCl$_2$ | t-BuMgCl | Dihexyl ether | Me(t-Bu)AsCl |
| MePCl$_2$ | AllylMgBr | Diheptyl ether | Me(allyl)PCl |

EXAMPLE 8

The procedure of Example 2 is repeated except that the solvent is tetraglyme. t-Butylarsine is the expected product.

What is claimed is:

1. A method of preparing one or more Group VA organometal compound comprising the step of reacting one or more organomagnesium halide compounds with one or more Group VA metal halide compounds in an ethereal solvent, wherein the ethereal solvent has a boiling point of $\geq 175°$ C.

2. The method of claim 1 wherein at least one Group VA metal halide compound has the formula $R^2R^3MX^1$, wherein $X^1$ is a halogen; M is a Group VA metal; and $R^2$ and $R^3$ are independently selected from hydrogen, halogen, $(C_1-C_{12})$ alkyl, $(C_2-C_{12})$alkenyl, $(C_2-C_{12})$alkynyl, and $(C_6-C_{20})$aryl.

3. The method of claim 1 wherein at least one organomagnesium halide compound has the formula $R^1MgX$, wherein $R^1$ is $(C_1-C_{12})$alkyl, $(C_2-C_{12})$alkenyl, $(C_2-C_{12})$ alkynyl, and $(C_6-C_{20})$aryl; and X is a halogen.

4. The method of claim 1 wherein at least one Group VA organometal compound is a Group VA organometal dihalide.

5. The method of claim 4 wherein the Group VA organometal dihalide has the formula $X_2M^1R^5M^2X_2$, wherein $M^1$ and $M^2$ are independently selected from arsenic and phosphorus, each X is independently selected from fluorine, chlorine, bromine and iodine, and $R^5$ is an alkylene or arylene group.

6. A method for preparing Group VA organometal hydride compounds comprising the steps of: a) reacting one or more organomagnesium halide compound with one or more Group VA halide compounds in an ethereal solvent to form one or more Group VA organometal halide compounds, wherein the ethereal solvent has a boiling point of $\geq 175°$ C.; and b) contacting the one or more Group VA organometal halide compounds with a reducing agent to form one or more Group VA organometal hydride compounds.

7. The method of claim 6 wherein at least one Group VA metal halide compound has the formula $R^2R^3MX^1$, wherein $X^1$ is a halogen; M is a Group VA metal; and $R^2$ and $R^3$ are independently selected from hydrogen, halogen, $(C_1-C_{12})$ alkyl, $(C_2-C_{12})$alkenyl, $(C_2-C_{12})$alkynyl, and $(C_6-C_{20})$aryl.

8. The method of claim 6 wherein at least one organomagnesium halide compound has the formula $R^1MgX$, wherein $R^1$ is $(C_1-C_{12})$alkyl, $(C_2-C_{12})$alkenyl, $(C_2-C_{12})$ alkynyl, and $(C_6-C_{20})$aryl; and X is a halogen.

9. The method of claim 6 wherein at least one Group VA organometal compound is a Group VA organometal dihalide.

10. The method of claim 9 wherein the Group VA organometal dihalide has the formula $X_2M^1R^5M^2X_2$, wherein $M^1$ and $M^2$ are independently selected from arsenic and phosphorus, each X is independently selected from fluorine, chlorine, bromine and iodine, and $R^5$ is an alkylene or arylene group.

* * * * *